(12) United States Patent
Fischer et al.

(10) Patent No.: US 6,536,070 B1
(45) Date of Patent: Mar. 25, 2003

(54) WINDSCREEN WIPER SYSTEM

(75) Inventors: Ernst Fischer, Gernbach (DE); Richard Hurst, Offenburg (DE); Claus Fleischer, Buehl (DE); Tino Boos, Baden-Baden (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/463,023

(22) PCT Filed: Dec. 14, 1998

(86) PCT No.: PCT/DE98/03667

§ 371 (c)(1),
(2), (4) Date: Apr. 26, 2000

(87) PCT Pub. No.: WO99/58379

PCT Pub. Date: Nov. 18, 1999

(30) Foreign Application Priority Data

May 9, 1998 (DE) .......................................... 198 20 789

(51) Int. Cl.⁷ .................................................. B60S 1/06
(52) U.S. Cl. .................. 15/250.31; 15/250.3; 296/192; 296/96.17; 248/316.6; 248/230.5
(58) Field of Search .......................... 15/250.3, 250.31, 15/250.27; 248/316.2, 316.6, 230.5; 296/96.17, 192; 74/42, 606 R

(56) References Cited

U.S. PATENT DOCUMENTS

| 5,222,706 A | * | 6/1993 | Hoshino .................. 15/250.31 |
| 5,878,631 A | * | 3/1999 | Muehlpforte et al. ...... 15/250.3 |
| 6,367,870 B1 | * | 4/2002 | Muehlpforte et al. .... 15/250.16 |

FOREIGN PATENT DOCUMENTS

| DE | 74 34 119 | 2/1975 |
| EP | 0 409 944 B1 | 5/1993 |

* cited by examiner

Primary Examiner—Gary K. Graham
(74) Attorney, Agent, or Firm—Michael J. Striker

(57) ABSTRACT

The invention is based on a windshield wiper system with a wiper motor (10), which is fastened to a vehicle body by means of a linkage housing (12) connected to the wiper motor and by means of a wiper support (48,50,52) with a hollow profile (86,88,90). The linkage housing (12) has at least one screw fitting (16,18), which is disposed spaced apart from a drive-side bearing dome (28) and extends in its direction. The hollow profile *86,88,90) of the wiper support is guided between the at least one screw fitting and the bearing dome and is supported against the circumference surfaces (30,32,34) of the at least one screw fitting and/or the bearing dome (28).

7 Claims, 4 Drawing Sheets

WINDSCREEN WIPER SYSTEM

BACKGROUND OF THE INVENTION

Wiper systems for motor vehicles are fastened to the body of a motor vehicle by means of a wiper support, a so-called mounting plate. The mounting plate supports a wiper drive mechanism with a wiper motor and a linkage built onto it whose drive shaft, as a rule by way of a crank and connecting rods, drives cranks that are connected to a drive shaft for each wiper. As a rule, the linkage housing is attached to a motor support of the mounting plate with three screws. The screws engage in protruding screw fittings of a drive-side housing cover with which the linkage housing is supported on the motor support.

The drive shaft of the wiper is supported in a wiper bearing whose bearing housing is fastened to the wiper support or formed onto it. This wiper support is attached to the vehicle body directly by way of the wiper bearing or by way of fastening eyelets that are formed onto the wiper bearing, the wiper support, and/or the motor support.

German utility model 74 34 119 has disclosed a wiper support that is made of a square tube to which a plate is welded that serves as a motor support. Wiper supports of this kind, often called tubular mounting plates or tubular frame systems, are very stable despite a lightweight construction. For cost reasons, a straight support tube is desirable since no prior bending work is required.

A wiper support has also been disclosed by EP 0 409 944 B1, in which a motor support connects tubular parts by way of form-fitting connections. The essentially straight tubular parts have noise-damping, frequency-filtering, or noise-absorbing intermediary parts inserted into them in order to damp noise that is transmitted by the wiper motor via the wiper support onto the wiper bearings and from there, into the vehicle body. A variant demonstrates that the motor support can be embodied in one piece with a housing cover of the linkage housing.

In addition, the journal "Werkstatt und Betrieb" [workshop and operation] Carl Hanser Verlag Munich, 1995, pp. 812 to 815, and the special edition from the journal "Metallumformtechnik" [metal shaping techniques], Claus Dannert Verlag, 1994, under the title "Prazisions-Werkstucke in Leichtbauweise, hergestellt durch Innenhochdruck-Umformen" [precision lightweight work pieces produced using internal high pressure shaping] have disclosed a process for shaping tubes into work pieces. This process, which is primarily used for the automotive industry, operates with high pressures. The tubular piece to be shaped is placed in a split molding tool which has the desired work piece mold incorporated into it. The molding tool, which is mounted in a press, is closed by means of a vertically acting press tappet. The tube ends are closed by closing tools, through which a pressure medium is supplied, which presses the tube walls against the inner tool mold. An axial pressure is exerted on the tube by horizontally acting tappets, which overlaps with the internal pressure. Consequently, the material which is required for the shaping is supplied not only from the wall thickness of the tube, but also through the shortening of the tube. The closing tools are guided so that they axially follow this shortening of the tube during the shaping. It is the subject of a prior patent application to also use a process of this kind for the manufacture of a tubular wiper support with different cross sectional shapes.

SUMMARY OF THE INVENTION

According to the invention, the hollow profile of the wiper support is guided between at least one screw fitting on one side and the bearing dome of the linkage housing on the other and is secured by means of a retention device, e.g. in the form of a cover plate, screw, or the like. It is supported against the circumference surfaces of the screw fittings and the bearing dome and against the counter support of the linkage housing over a longer region, which extends in the longitudinal direction of the screw fittings. It is therefore secured against rotation. This can be achieved by virtue of the fact that the outer contour of the hollow profile follows the inclination of the screw fittings and the bearing dome. The inclinations of the circumference surfaces of the screw fittings and the bearing dome depend primarily on the manufacturing process when the linkage housing is produced for example by means of a casting process.

In the axial direction, the hollow profile is likewise secured in relation to the linkage housing in a form-fitting manner, by virtue of the fact that it has indentations in the vicinity of the screw fittings and/or the bearing dome, and these indentations partly encompass the screw fittings or the bearing dome. With otherwise circular cross sectional profiles, the indentations also produce a longer contact of the hollow profile along the screw fittings or the bearing dome.

Another possibility for axially securing the hollow profile in relation to the linkage housing is comprised in that the hollow profile has a continuous cross sectional reduction in the vicinity of the screw fittings and the bearing dome, whose shoulders rest against the circumference contour of the screw fittings and/or against the edges of the retention device. In order to embody the form-fitting connections so that it is free of play, is advantageous to clamp the hollow profile between the screw fittings, the bearing dome, and the retention device by means of a certain initial stress.

According to one embodiment of the invention, the screw fittings and the bearing dome are connected to each other by means of housing ribs. The housing ribs on the sides of the hollow profile that are respectively remote from the screw fittings and the bearing dome constitute a counter support for the hollow profile in relation to the screw fittings and the bearing down. This counteracts the stress concentrations of the indentations and in addition, the forces are introduced into the linkage housing in a more uniform and favorable fashion so that a very stable connection of the wiper motor and the wiper linkage is achieved.

The wiper support of the wiper system according to the invention is comprised essentially of a dimensionally stable hollow profile with a round or polygonal cross sectional profile, which is advantageously produced using an internal high pressure shaping process and whose ends support the wiper bearing. A separate motor support is not required. The wiper support is also distinguished by a continuous hollow profile in the vicinity of the wiper motor. This results in a high degree of strength and dimensional stability as well as a low manufacture and assembly cost since connecting elements or a welding process to connect the motor support to the wiper support is no longer necessary.

The linkage housing of the wiper system according to the invention is only slightly modified so that on the one hand, it can be attached to the hollow profile of the wiper support by means of the simple retention device and on the other hand is suitable for an attachment to the usual wiper support with a conventional motor support by means of the screw fittings.

In the wiper system according to the invention, the retention device can also be used to support the wiper support by virtue of the fact that it has integrated supports, e.g. a fastening eyelet, for attachment to the vehicle body.

BRIEF DESCRIPTION OF THE DRAWINGS

Other advantages ensue from the following description of the drawings. The drawings depict exemplary embodiments of the invention. The drawings, the description, and the claims contain numerous features in combination. One skilled in the art will also suitably consider the features individually and will combine them into other meaningful combinations.

DESCRIPTION OF THE PREFERRED EMBODIMENTS

Figure 1:
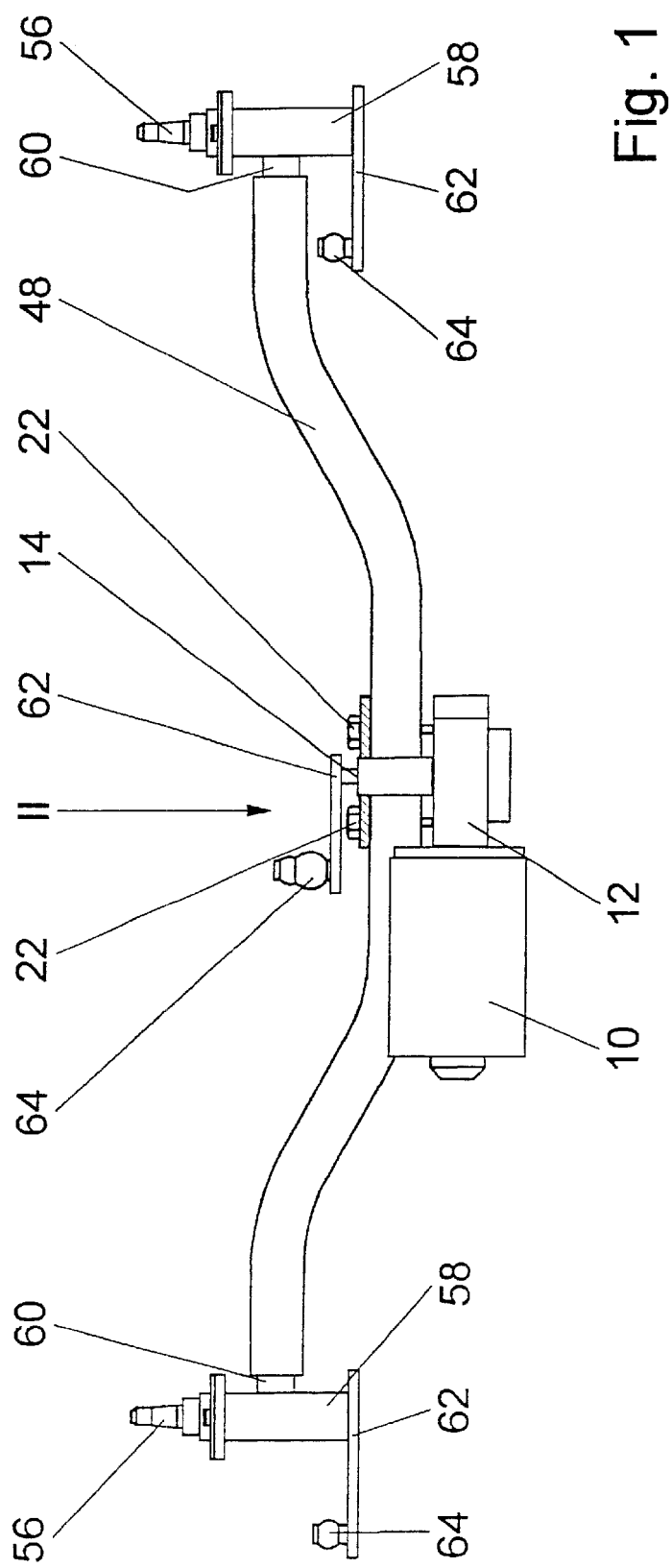
FIG. 1 gives a schematic overview of a wiper system without wipers.

The wiper system includes a wiper motor 10 with a linkage housing 12 mounted to it, which is screwed to a wiper support 48, 50, 52 by means of three screws 22. By way of a driven shaft 14, the wiper motor 10 drives a crank 62 with an articulation ball 64 which is connected via articulating rods, not shown in detail, to corresponding cranks 62 and articulation balls 64. These cranks 62 are attached to drive shafts 56 which are supported in bearing housings 58 and are mounted to the wipers that are not shown. The bearing housings 58 are pressed with their connecting pieces 60 into the ends of the wiper support 48, 50, 52 and are secured there by means of frictional connection and/or positive fit.

The wiper support 48, 50, 52 has a hollow profile 86, 88, 90, which is suitably manufactured using an internal high pressure process. This permits different cross sectional profiles to be produced in a simple manner, e.g. round and polygonal profiles, which can, however, also vary in the longitudinal direction in accordance with the stresses and installation conditions.

The linkage housing 12 is secured to the wiper support 48, 50, 52 by virtue of the fact that the hollow profile 86, 88, 90 of the wiper support 48, 50, 52 is guided between a bearing dome 28, in which the drive shaft 14 is supported, and two screw fittings 16 and 18, which are disposed offset toward both sides of the bearing dome 28 in the axial direction of the wiper support 48, 50, 52. As a result of the manufacturing process, the circumference surfaces 30, 32, 34 of the screw fittings 16, 18 and the bearing dome 28 have an inclination 36 with an inclination angle 38. In the vicinity of the screw fittings 16 and 18 and the bearing dome 28, the hollow profile 86, 88, 90 is adapted to the inclinations 36 so that it rests against the screw fittings 16, 18 and the bearing dome 28 over a longer region 24, 26 and is consequently secured against rotation.

Figure 2:
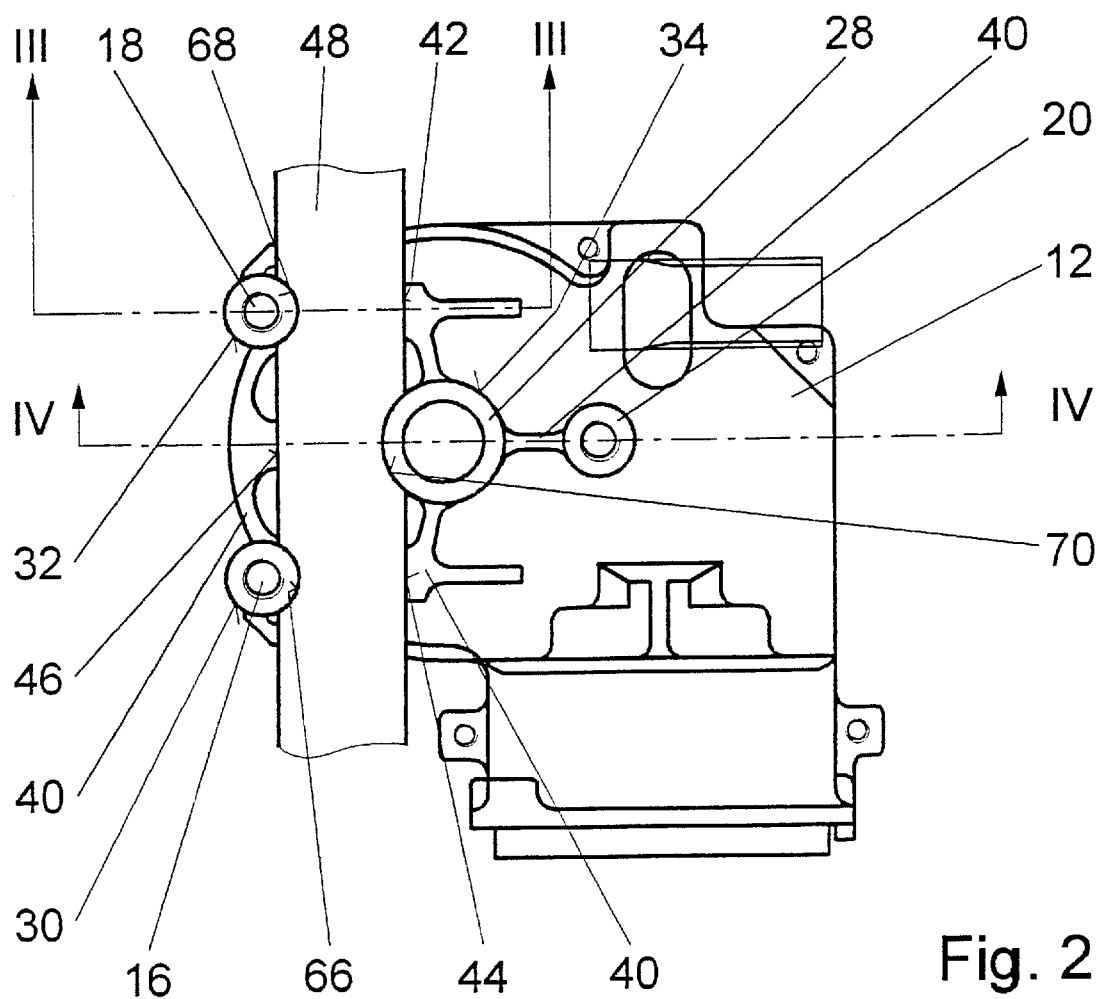
FIG. 2 is an enlarged top view without a retention device, in the direction of the arrow II in FIG. 1.
Figure 3:
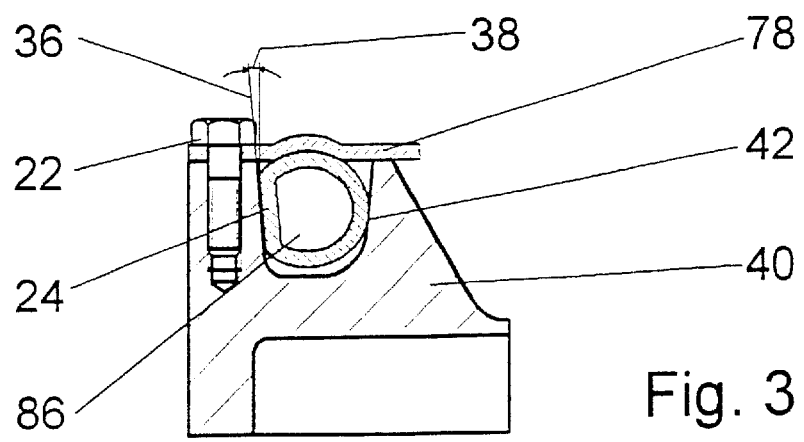
FIG. 3 is a partial section corresponding to the line III—III in FIG. 2.
Figure 4:
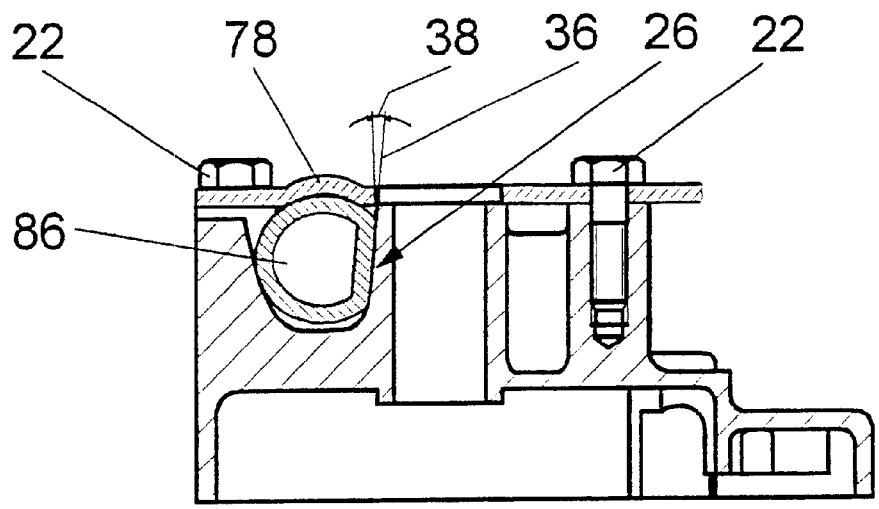
FIG. 4 is a partial section corresponding to the line IV—IV in FIG. 2.

In the embodiment according to FIGS. 2, 3, 4, the wiper support 48 has indentations 66, 68, 70, which nestle against the circumference surfaces 30, 32, 34 of the screw fittings 16 and 18 and the bearing dome 28. As a result, the wiper support 48 is axially fixed in relation to the linkage housing 12.

The wiper support 48, 50, 52 is secured by a retention device 78 in the form of a cover plate between the screw fittings 16 and 18 on the one hand and the bearing dome 28 on the other, and is clamped by the screws 22 in a prestressed, play-free manner. In order to introduce the securing forces into the linkage housing 12 in a uniform fashion and in order to minimize the stress concentration on the wiper support 48, 50, 52, the linkage housing 12 has housing ribs 40 for reinforcement which constitutes counter supports 42, 44, 46 in the vicinity of the screw fittings 16 and 18 and the bearing dome 28. These can be used alone or in combination with the screw fittings 16 and 18 and the bearing dome 28 as a rotation prevention means by virtue of the fact that with a region, they rest against the wiper support 48, 50, 52 in the longitudinal direction. Consequently, a long-lasting play-free connection between the wiper support 48, 50, 52 and the linkage housing 12, together with the wiper motor 10, is assured through simple means and without a high manufacturing cost.

In order to connect the wiper support 48, 50, 52 in a favorable manner to the body of a vehicle, it is suitable to provide an additional support point in the vicinity of the linkage housing 12 and the wiper motor 10, e.g. in the form of a support 84 embodied as a fastening eyelet which is integrated into the retention device 78.

Figure 5:
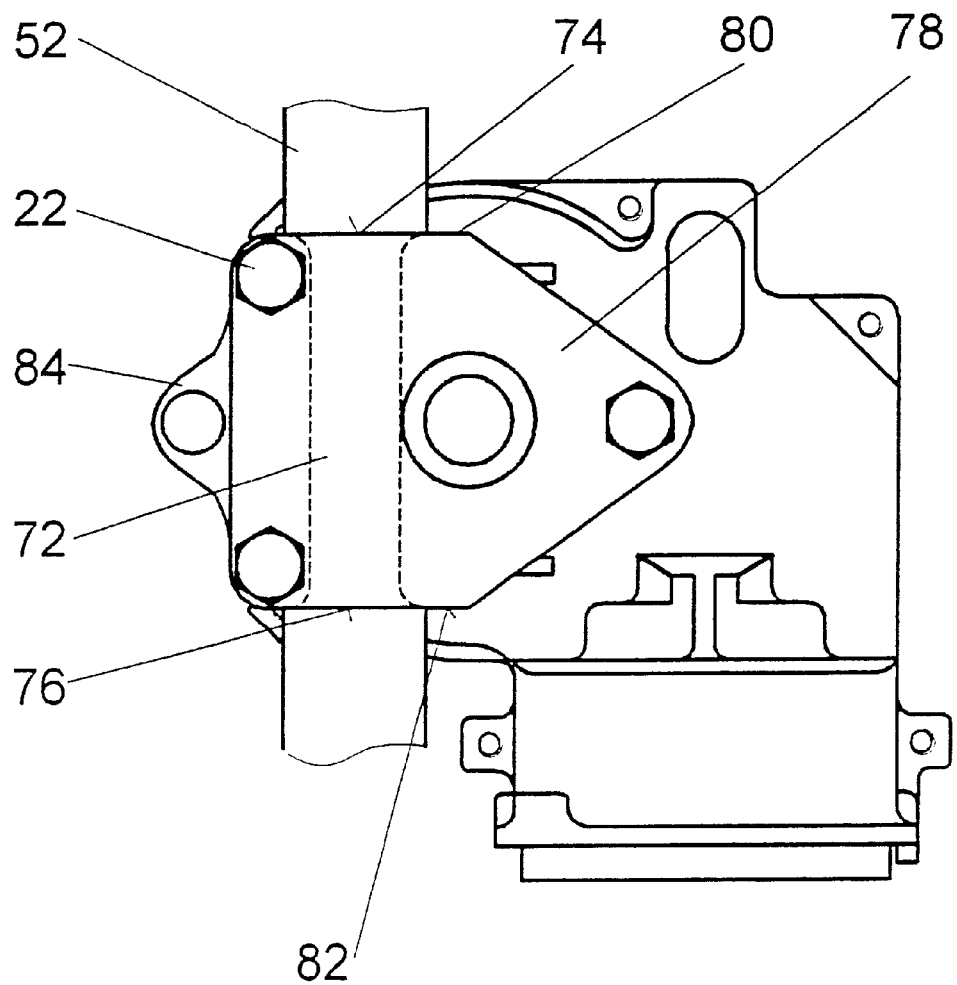
FIG. 5 shows a variant to FIG. 2 with a retention device.
Figure 6:
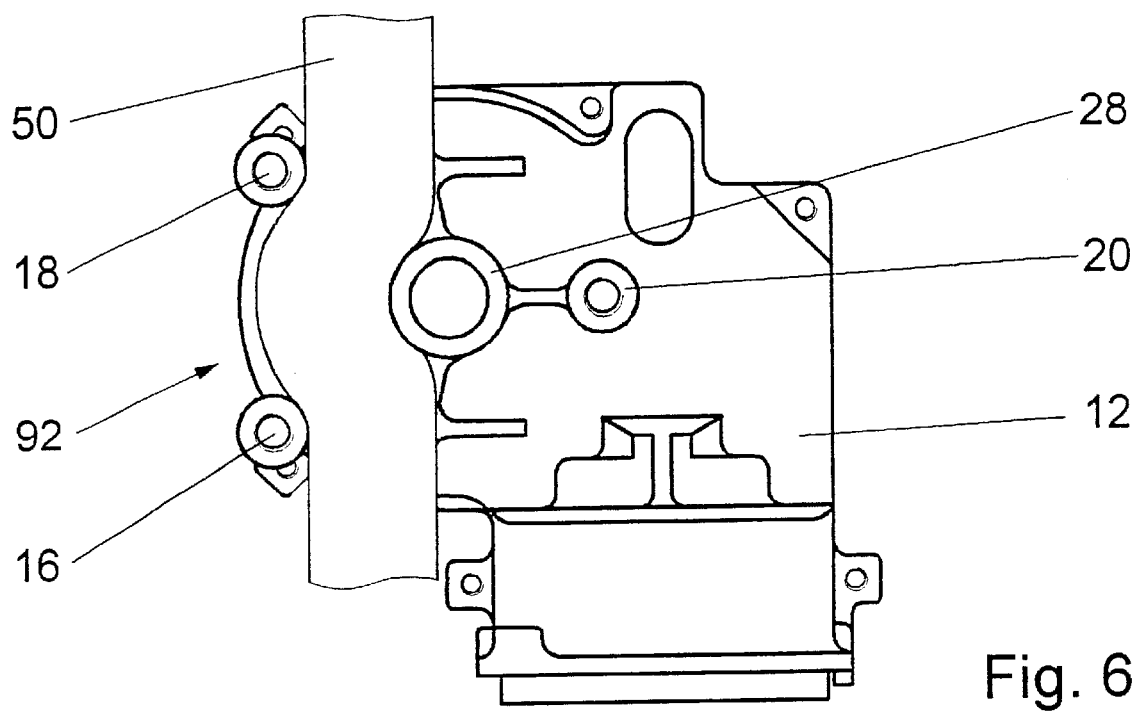
FIG. 6 shows another variant to FIG. 2.

In the embodiment according to FIG. 5, the wiper support 52 has a continuous cross sectional reduction 72 between the screw fittings 16 and 18, which corresponds to the indentations 66, 68, 70. The flanks of the cross sectional reduction 72 rest in a rotationally fixed manner against the regions 24, 26 of the circumference surfaces 30, 32, and 34, while shoulders 74 and 76 on the end of the cross sectional reduction 72 provide the axial retention by virtue of the fact that they rest of against the circumference surfaces 30 and 32 of the screw fittings 16 and 18 and/or against the edges 80 and 82 of the retention device 78.

In order to keep the cross section of the wiper support 50 as large as possible in the critical fastening regions between the screw fittings 16 and 18, it is advantageous that the wiper support 50 in this instance has a right-angle bend 92, which is simultaneously used to axially fix the wiper support 50 in relation to the linkage housing 12.

Figure 7:
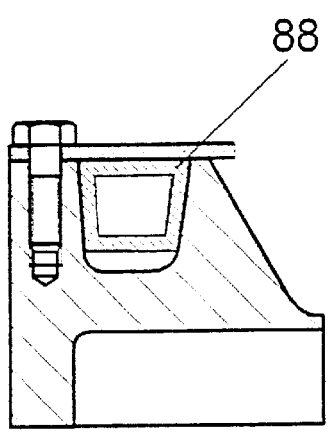
FIG. 7 shows a variant to FIG. 3 with a polygonal cross sectional profile.
Figure 8:
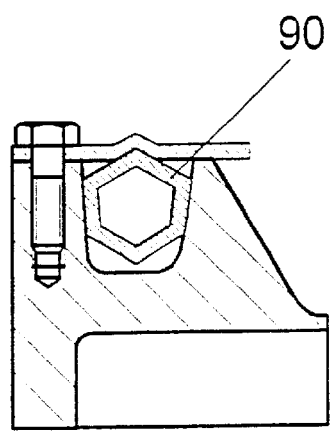
FIG. 8 shows a variant to FIG. 7.

The wiper support 48, 50, 52 can have a hollow profiles 86, 88, 90 with different cross sectional contours, e.g. rounded sections, which are essentially circular or elliptical, or polygons, as shown in FIGS. 7 and 8. As a result, the wiper support 48, 50, 52 can be adapted to a wide variety of stresses and installation conditions.

What is claimed is:

1. A wiper system, comprising a wiper motor fastenable to a vehicle body by a linkage housing connected to said wiper motor and by a wiper support with a hollow profile, said linkage housing having at least one screw fitting disposed spaced apart from a drive-side bearing dome, said wiper support has spaced opposite sides, said hollow profile of said wiper support being guided between said at least one screw fitting at one of said sides and said bearing dome at the other of said sides, being supported against circumferential surfaces of at least one element selected from the group consisting of said at least one screw fitting and said bearing dome by a region extending in a longitudinal direction of said screw fitting, and being secured by at least one retention device.

2. A wiper system as defined in claim 1, wherein said at least one screw fitting and said bearing dome are connected by housing ribs which, on a side of said hollow profile remote from said screw fitting and said bearing dome serve as counter supports to said screw fitting and said bearing dome, said hollow profile being supported against said at least one screw fitting, said bearing dome, and at least one of said counter supports by a region extending in a longitudinal direction of said screw fitting.

3. A wiper system as defined in claim 2, wherein said hollow profile has indentations in a vicinity of an element selected from the group consisting of said at least one screw fitting, said bearing dome, and at least one of said counter supports.

4. A wiper system as defined in claim 2, wherein said hollow profile is clamped between an element selected from the group consisting of said at least one retention device, said at least one screw fitting, said bearing dome, and at least one of said counter supports.

5. A wiper system as defined in claim 1, wherein in a vicinity of said at least one screw fitting and said bearing dome, said hollow profile having a continuous transverse cross-sectional reduction with shoulders securing said hollow profile in relation to said linkage housing in a longitudinal direction.

6. A wiper system as defined in claim 1, wherein said retention device has an integrated support for attachment to the vehicle body.

7. A wiper system as defined in claim 1, wherein said hollow profile is a hollow profile manufactured using an internal high-pressure shaping process.

* * * * *